US010517520B2

(12) United States Patent
Bott et al.

(10) Patent No.: US 10,517,520 B2
(45) Date of Patent: Dec. 31, 2019

(54) METHOD AND SYSTEM FOR CORRELATING AN IMAGE CAPTURING DEVICE TO A HUMAN USER FOR ANALYSIS OF COGNITIVE PERFORMANCE

(71) Applicant: Neurotrack Technologies, Inc., Redwood City, CA (US)

(72) Inventors: Nick Bott, Menlo Park, CA (US); Alexander R. Lange, Redwood City, CA (US); Rob Cosgriff, Redwood City, CA (US); Roger Hsiao, Mountain View, CA (US); Brad Dolin, San Franscisco, CA (US)

(73) Assignee: Neurotrack Technologies, Inc., Redwood City, CA (US)

( * ) Notice: Subject to any disclaimer, the term of this patent is extended or adjusted under 35 U.S.C. 154(b) by 217 days.

(21) Appl. No.: 15/809,880

(22) Filed: Nov. 10, 2017

(65) Prior Publication Data
US 2018/0125404 A1 May 10, 2018

Related U.S. Application Data

(60) Provisional application No. 62/420,521, filed on Nov. 10, 2016.

(51) Int. Cl.
*A61B 5/16* (2006.01)
*H04N 7/18* (2006.01)
(Continued)

(52) U.S. Cl.
CPC .............. *A61B 5/163* (2017.08); *A61B 5/165* (2013.01); *A61B 5/4088* (2013.01);
(Continued)

(58) Field of Classification Search
CPC ....... A61B 5/163; A61B 5/165; A61B 5/4088; A63F 13/213; A63F 13/822; A63F 13/85;
(Continued)

(56) References Cited

U.S. PATENT DOCUMENTS 8,506,080 B2 * 8/2013 Raffle .................... A61B 3/113
351/209
2003/0146372 A1 * 8/2003 Hsish ................ H01L 27/14609
250/214.1
(Continued)

FOREIGN PATENT DOCUMENTS

WO 2016125042 A1 8/2016

OTHER PUBLICATIONS

International Search Report and Written Opinion for PCT/US2017/061183 dated Feb. 5, 2018.

*Primary Examiner* — Sath V Perungavoor
*Assistant Examiner* — Yong Joon Kwon
(74) *Attorney, Agent, or Firm* — Richard T. Ogawa; Ogawa P.C.

(57) ABSTRACT

A method capturing eye movement data for detection of cognitive anomalies, includes a computer application displaying a frame on a display, capturing and displaying a video image of a user's face and eyes, while the user aligns the face to the frame, capturing and processing the face image to initiate an image eye movement capture process, outputting an indication on a display and moving the indication spatially to one of a plurality of images, capturing a video of each user eye, to track the position of the indication of the display, the image of each eye comprising a sclera portion, an iris portion, and a pupil portion, parsing the video to determine a reference images corresponding to eye positions, capturing the user's eyes while the user views familiar and novel images, and correlating the images of the user's (Continued)

eyes to the familiar or novel images using the reference images.

10 Claims, 8 Drawing Sheets

(51) Int. Cl.
| | |
|---|---|
| *H04N 5/232* | (2006.01) |
| *G06T 7/11* | (2017.01) |
| *G06F 3/01* | (2006.01) |
| *A61B 5/00* | (2006.01) |
| *A63F 13/822* | (2014.01) |
| *A63F 13/85* | (2014.01) |
| *G09B 19/18* | (2006.01) |
| *G09B 19/00* | (2006.01) |
| *A63F 13/213* | (2014.01) |

(52) U.S. Cl.
CPC ............ *A63F 13/822* (2014.09); *A63F 13/85* (2014.09); *G06F 3/013* (2013.01); *G06T 7/11* (2017.01); *G09B 19/00* (2013.01); *G09B 19/18* (2013.01); *H04N 5/23293* (2013.01); *H04N 7/185* (2013.01); *A63F 13/213* (2014.09)

(58) Field of Classification Search
CPC ...... G06F 3/013; G06K 9/00; G06K 9/00255; G06K 9/0061; G06K 9/00832; G06T 2207/30041; G06T 7/11; G06T 7/248; G09B 19/00; G09B 19/18; H04N 5/23206; H04N 5/23222; H04N 5/23293; H04N 7/183; H04N 7/185

See application file for complete search history.

(56) References Cited

U.S. PATENT DOCUMENTS

| | | |
|---|---|---|
| 2008/0166025 A1 | 7/2008 | Thorne |
| 2008/0267459 A1* | 10/2008 | Nakada ................... G09B 19/00 382/118 |
| 2009/0016574 A1* | 1/2009 | Tsukahara ............... A61B 5/117 382/117 |
| 2010/0053555 A1* | 3/2010 | Enriquez ................. A61B 3/113 351/210 |
| 2010/0207877 A1 | 8/2010 | Woodard |
| 2011/0150280 A1* | 6/2011 | Tsuji ....................... G06T 7/248 382/103 |
| 2015/0145777 A1* | 5/2015 | He ........................ G06K 9/0061 345/158 |
| 2015/0220157 A1* | 8/2015 | Marggraff ............... G06F 3/017 345/156 |
| 2015/0373303 A1 | 12/2015 | Visosky |
| 2017/0236337 A1* | 8/2017 | Devries ................. G06F 3/0304 345/419 |
| 2019/0150819 A1* | 5/2019 | Charvat .................... A61B 5/16 |

* cited by examiner

METHOD AND SYSTEM FOR CORRELATING AN IMAGE CAPTURING DEVICE TO A HUMAN USER FOR ANALYSIS OF COGNITIVE PERFORMANCE

CROSS-REFERENCE TO RELATED CASES

The present invention is a non-provisional of U.S. Patent Application No. 62/420,521 filed Nov. 10, 2016 and that application is incorporated by reference herein, for all purposes.

BACKGROUND

The present invention relates to methods and apparatus for diagnosing cognitive impairment of a subject. More specifically, the present invention relates to methods an apparatus for acquisition of eye movement data.

According to embodiments of the present invention, techniques for processing information associated with eye movement using web based image-capturing devices is disclosed. Merely by way of example, the invention can be applied to analysis of information for determining cognitive performance of subjects.

Historically, recognition memory of a subject has been assessed through conventional paper-pencil based task paradigms. Such tests typically occur in a controlled environment (e.g. laboratory, doctor's office, etc.) under the guidance of a test administrator using expensive (e.g. $10k-$80K) systems. Such tests also require the subject to travel to the laboratory and spend over an hour preparing for and taking such tests. Typically, a test administrator shows a series of visual stimuli to subjects at a certain frequency and rate. After the exposure phase the user waits for a time delay of over twenty-five minutes before the test administrator tests the subject's recall of the visual stimuli. In addition to the visual stimuli and the test administrator, visual recognition memory paradigms also require response sheets to facilitate administrator scoring. Although effective, conventional paradigms are expensive, cumbersome, and subjective.

From the above, it is seen that techniques for improving acquisition of eye movement data are highly desired.

SUMMARY

According to the present invention, techniques for processing information associated with eye movement using web based image-capturing devices. Merely by way of example, the invention can be applied to analysis of information for determining cognitive performance of subjects.

According to one aspect of the invention a method of processing information including aligning eye movement with an image capturing device for detection of cognitive anomalies is described. One method includes initiating an application, under control of a processor, to output an image of a frame on a display device to a user, the display device being coupled to the processor, the processor being coupled to a communication device coupled to a network of computers, the network of computers being coupled to a server device, initiating a camera coupled to the application to capture a video image of a face of a user, the face of the user being positioned by the user viewing the display device, and displaying the video of the image of the face of the user (e.g. including their eyes, pupils, etc.) on the display device within a vicinity of the frame being displayed. A process includes positioning the face of the user within the frame to align the face to the frame, and capturing an image of the face of the user, processing captured information regarding the image of the face to initiate an image capturing process of eye movement of the user, and outputting an indication on a display after initiation of the image capturing process; and moving the indication spatially to one of a plurality of images being displayed on the display device. A technique includes capturing a video of at least one eye of the human user, while the user's head/face is maintained within the viewing display of the device (e.g. visible to the camera), and one or both eyes of the user moves to track the position of the indication of the display, the image of each eye comprising a sclera portion, an iris portion, and a pupil portion, parsing the video to determine a first reference image corresponding to a first eye position for a first spatial position for the indication; and a second reference image corresponding to a second eye position for a second spatial position of the indication, and correlating each of the other plurality of images to either the first reference image or the second reference image. In various embodiments, the parsing steps may be performed on a user's computing device, or by a remote server.

According to another aspect of the invention, a method for processing information using a web camera, the web camera being coupled to a computing system is disclosed. One technique includes placing a user in front of a display device coupled to the computing system, the computing system being coupled to a worldwide network of computers, initiating a Neurotrack application stored on a memory device of the computing system and initiating the web camera by transferring a selected command from the Neurotrack application. A process may include capturing an image of a facial region of the user positioned in front of the display device, retrieving a plurality of test images from the memory device coupled to the computing system, the plurality of test images comprising a first pair of images, a second pair of images, a third pair of images, etc. (e.g. twentieth pair of images), each of the pair of images being related to each other, and displaying the first pair of the test images on the display device to be viewed by the user. A method may include capturing a plurality of first images associated with a first eye location while the user is viewing the first pair of test images, repeating the displaying of the pairs of images, while replacing one of the previous pairs of images, and capturing of images for a plurality of second pair of images to the twentieth pair of images, each of which while the user is viewing the display device, and capturing a fixation from an initial point having four regions within a vicinity of the initial point during the displaying of the pairs of images, while replacing the previous pair of images, each of the four regions within about one degree visual angle from the initial point, and an associated saccade with the fixation. A process may include processing information to filter the saccade, determining a visual preference using the fixation on the replaced image from the plurality of images; and using the visual preference information to provide the user with feedback.

According to another aspect of the invention, a method for playing a matching game on a host computer is disclosed. One technique may include uploading from the host computer to a remote computer system, a computer network address for a plurality of static images, wherein the plurality of static images comprises a first plurality of static images and a second plurality of static images. A method may include uploading from the host computer to the remote computer system, remote computer system executable software code including: first remote computer system executable software code that directs the remote computer system to display on a display of the remote computer system to a player, only static images from the first plurality of static images but not static images from the second plurality of static images, wherein each of the static images from the first plurality of static images is displayed upon at most half of the display for a first predetermined amount of time, second remote computer system executable software code that directs the remote computer system to inhibit displaying on the display of the remote computer system to the player, at least one static image from the first plurality of static images to the player, for a second predetermined amount of time, third remote computer system executable software code that directs the remote computer system to simultaneously display on the display of the remote computer system to the player, a first static image from the first plurality of static images and a second static image from the second plurality of static images, wherein the first static image and the second static image are displayed upon at most half of the display for a third predetermined amount of time, fourth remote computer system executable software code that directs the remote computer system to capture using a web camera of the remote computer system video data of the player, wherein the video data captures eye movements of the player while the display of the remote computer system is displaying to the player the first static image and the second static image, fifth remote computer system executable software code that directs the remote computer system to create edited video data from a subset of the video data in response to a pre-defined two dimensional area of interest from the video data, wherein the edited video data has a lower resolution than the video data, and sixth remote computer system executable software code that directs the remote computer to provide to the host computer, the edited video data. A process may include determining with the host computer a first amount of time representing an amount of time the player views the first static image and a second amount of time representing an amount of time the player views the second static image, in response to the edited video data, determining with the host computer a viewing relationship for the player between the second amount of time and the first amount of time, in response to the first amount of time and the second amount of time, and determining with the host computer whether the viewing relationship for the player between the second amount of time and the first amount of time exceeds a first threshold and generating a success flag in response thereto. A technique may include providing from the host computer to the remote computer system, an indication that the player is successful, in response to the success flag.

The above embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment implementations are illustrative, rather than limiting.

DETAILED DESCRIPTION

Figure 1A:
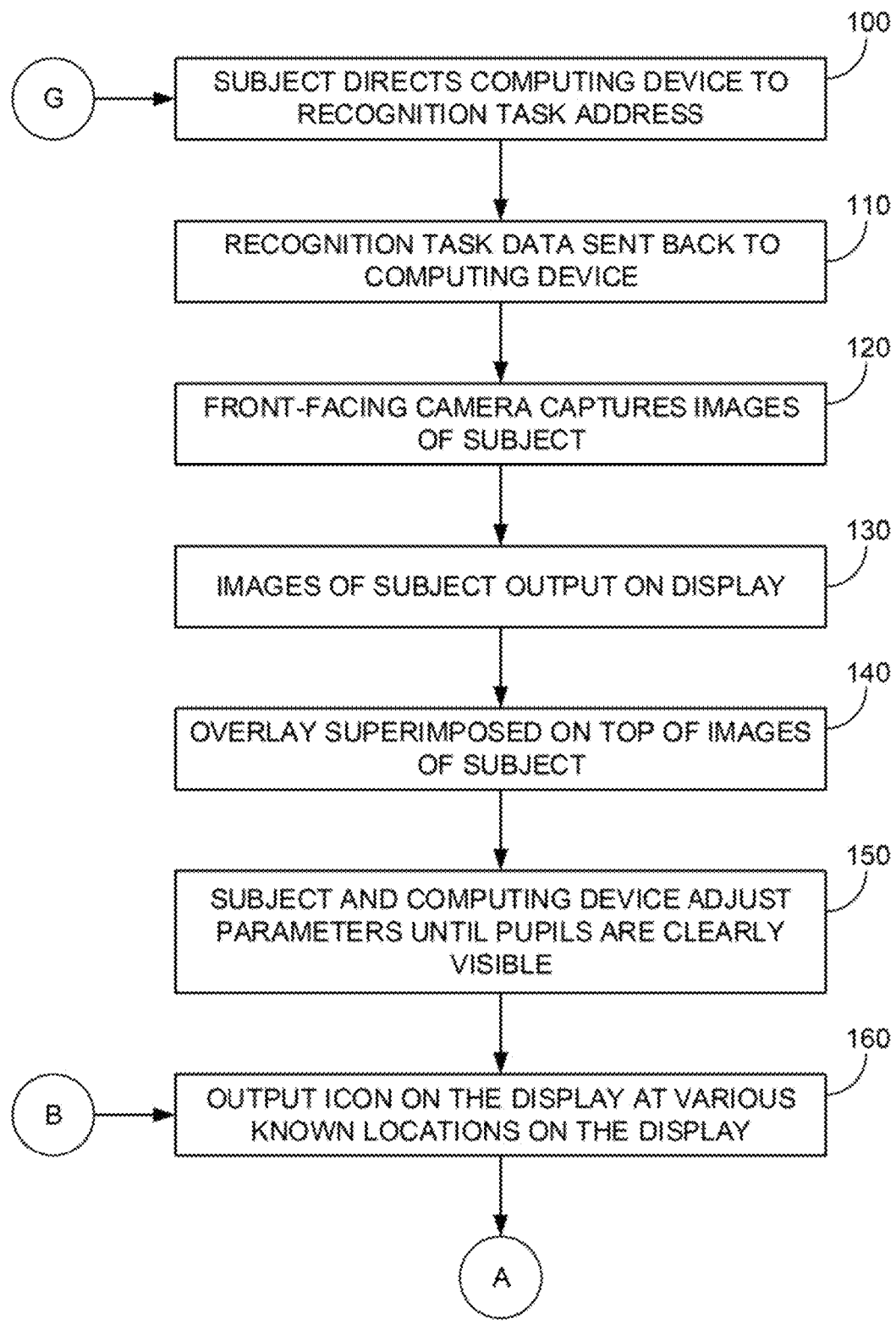
FIGS. 1A-E illustrate a flow diagram according to an embodiment of the present invention.
Figure 1B:
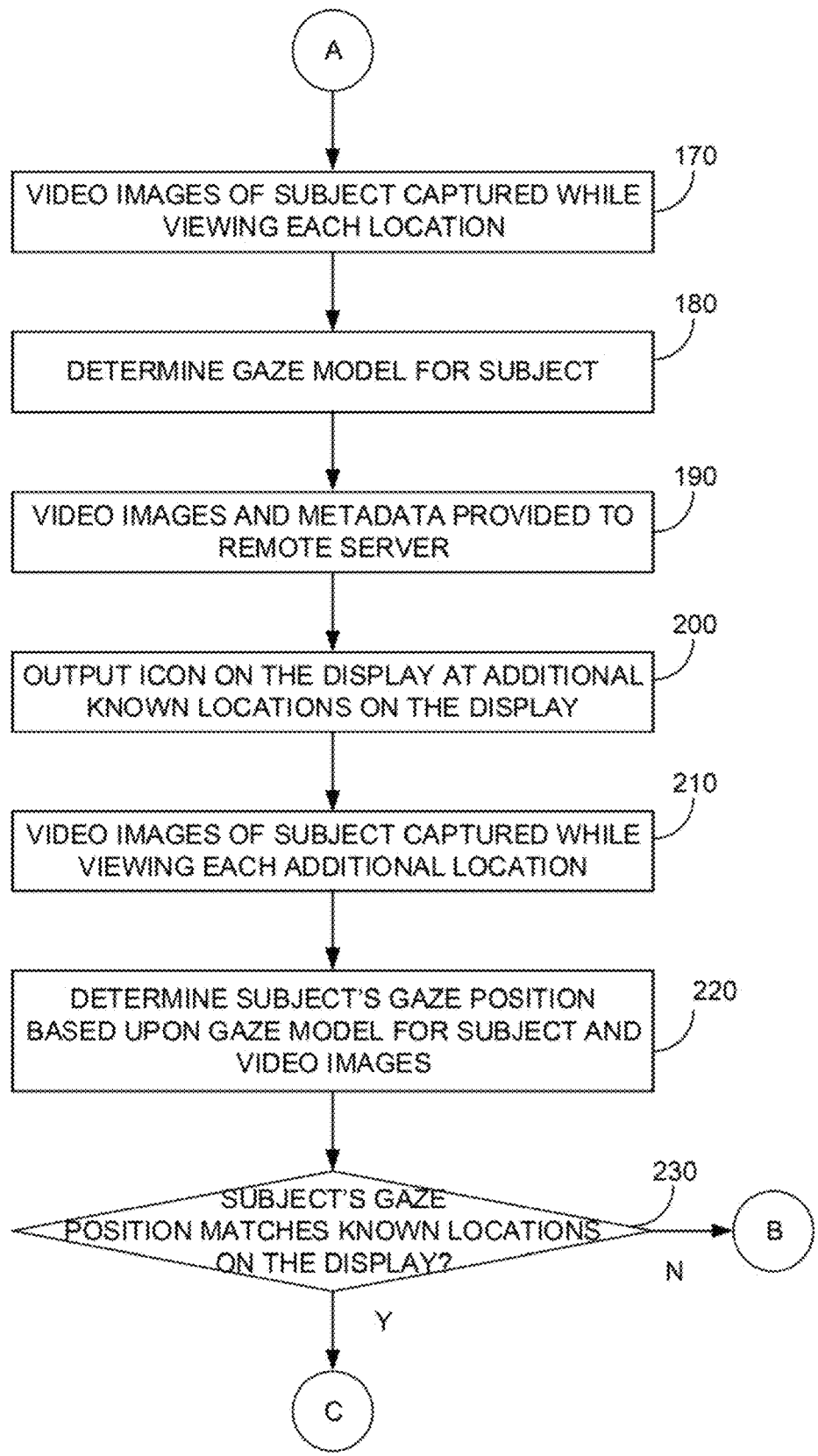
Figure 1C:
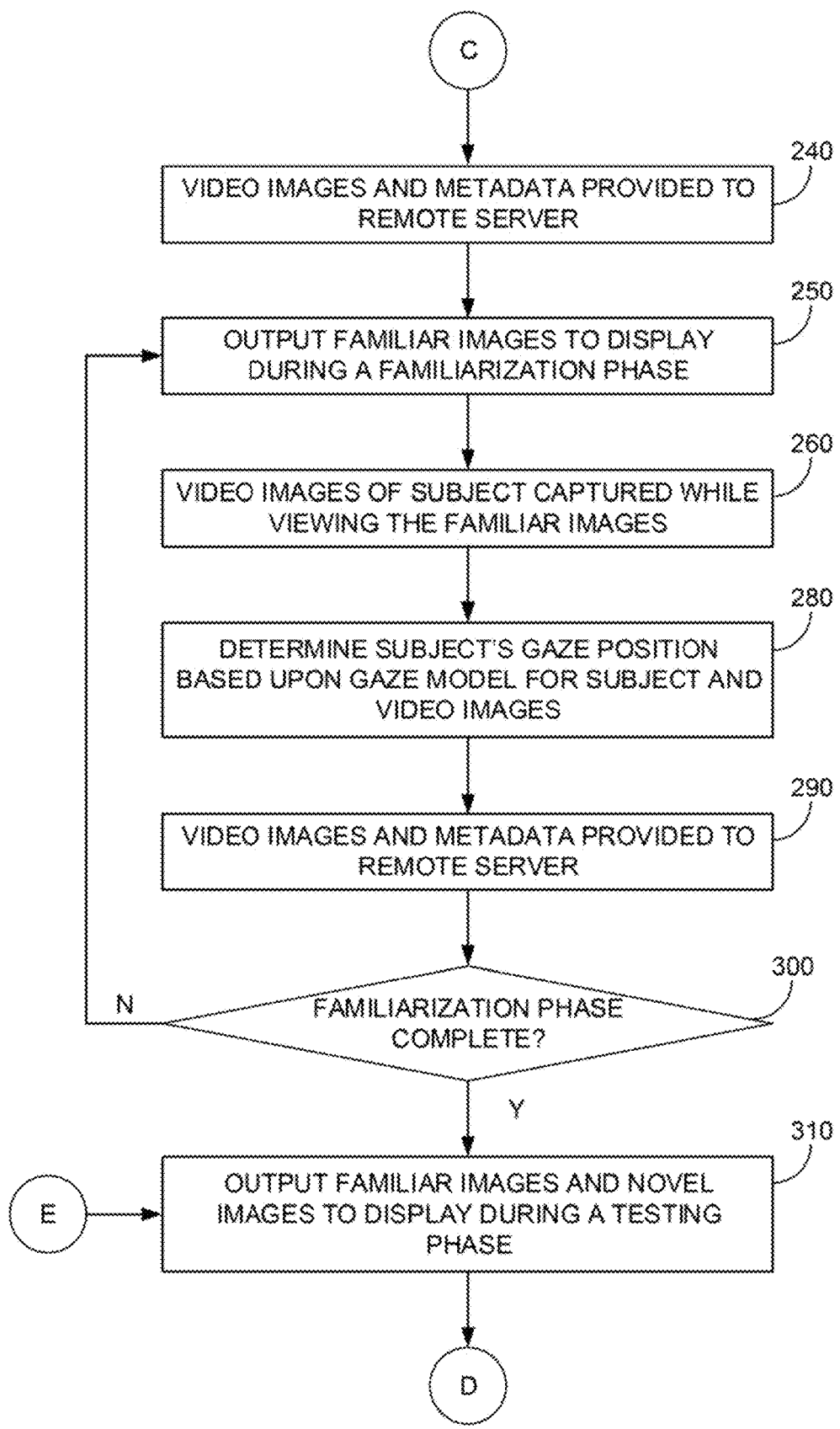
Figure 1D:
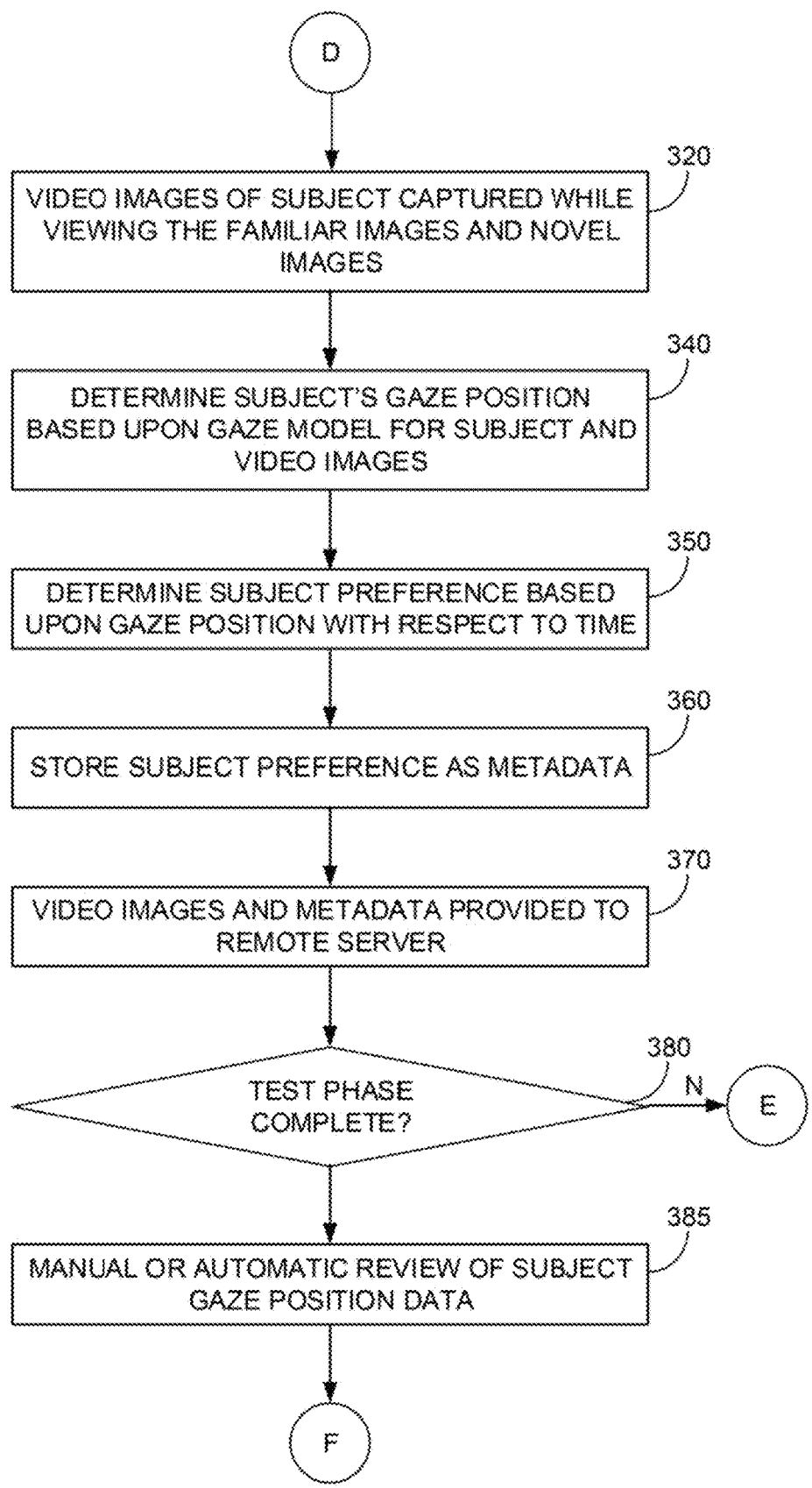
Figure 1E:
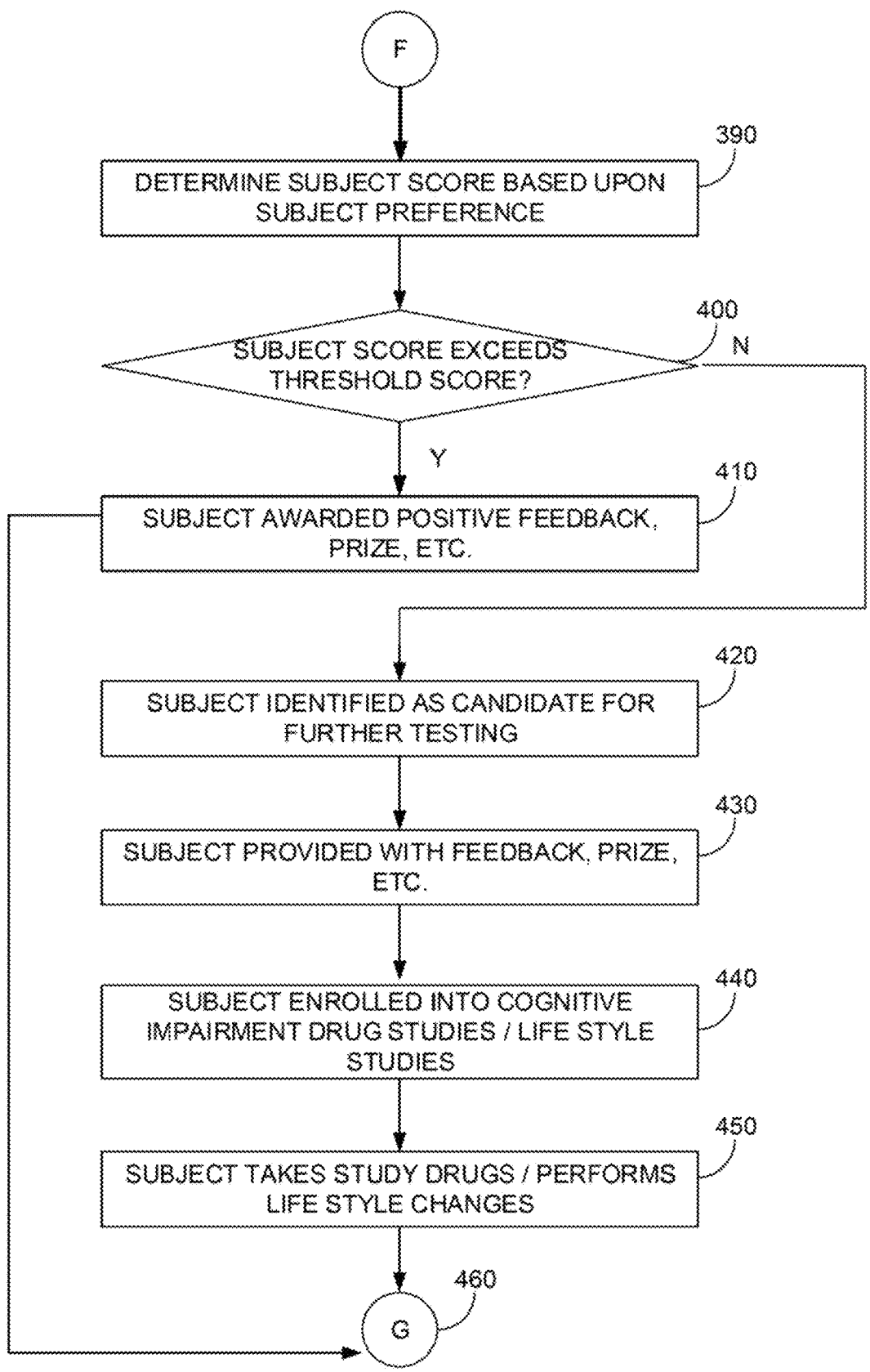

According to the present invention, techniques for processing information associated with eye movement using web based image-capturing devices. Merely by way of example, the invention can be applied to analysis of information for determining cognitive diseases.

Without limiting any of the interpretations in the claims, the following terms have been defined.

Choroid: Layer containing blood vessels that lines the back of the eye and is located between the retina (the inner light-sensitive layer) and the sclera (the outer white eye wall).

Ciliary Body: Structure containing muscle and is located behind the iris, which focuses the lens.

Cornea: The clear front window of the eye which transmits and focuses (i.e., sharpness or clarity) light into the eye. Corrective laser surgery reshapes the cornea, changing the focus.

Fovea: The center of the macula, which provides the sharp vision. Iris: The colored part of the eye which helps regulate the amount of light entering the eye. When there is bright light, the iris closes the pupil to let in less light. And when there is low light, the iris opens up the pupil to let in more light.

Lens: Focuses light rays onto the retina. The lens is transparent, and can be replaced if necessary. Our lens deteriorates as we age, resulting in the need for reading glasses. Intraocular lenses are used to replace lenses clouded by cataracts.

Macula: The area in the retina that contains special light-sensitive cells. In the macula these light-sensitive cells allow us to see fine details clearly in the center of our visual field. The deterioration of the macula is commonly occurs with age (age related macular degeneration or ARMD).

Optic Nerve: A bundle of more than a million nerve fibers carrying visual messages from the retina to the brain. (In order to see, we must have light and our eyes must be connected to the brain.) Your brain actually controls what you see, since it combines images. The retina sees images upside down but the brain turns images right side up. This reversal of the images that we see is much like a mirror in a camera. Glaucoma is one of the most common eye conditions related to optic nerve damage.

Pupil: The dark center opening in the middle of the iris. The pupil changes size to adjust for the amount of light available (smaller for bright light and larger for low light). This opening and closing of light into the eye is much like the aperture in most 35 mm cameras which lets in more or less light depending upon the conditions.

Retina: The nerve layer lining the back of the eye. The retina senses light and creates electrical impulses that are sent through the optic nerve to the brain.

Sclera: The white outer coat of the eye, surrounding the iris.

Vitreous Humor: The, clear, gelatinous substance filling the central cavity of the eye.

Novelty preference: Embodiments of the present invention assess recognition memory through comparison of the proportion of time an individual spends viewing a new picture compared to a picture they have previously seen, i.e., a novelty preference. A novelty preference, or more time spent looking at the new picture, is expected in users (e.g. individuals, test subjects, patients) with normal memory function. By contrast, users with memory difficulties (cognitive impairments) are characterized by more equally distributed viewing times between the novel and familiar pictures. The lack of novelty preference suggests a cognitive dysfunction with regards to what the subject has already viewed.

Cameras capturing images/videos (e.g. web cameras) are increasingly part of the standard hardware of smart phones, tablets and laptop computers. The quality and cost of these devices has allowed for their increased use worldwide and are now a standard feature on most smart devices, including desktop and laptop computers, tablets, and smart phones. The inventor of the present invention has recognized that it is possible to incorporate the use of such web cameras for visual recognition tasks. In particular, the inventor has recognized that using such web cameras, he can now provide web-based administration of visual recognition tasks.

Advantages to embodiments of the present invention include that such visual recognition tasks become very convenient for subjects. Subjects need not travel to and from an administration facility (e.g. laboratory, doctor's office, etc.) and the subjects can have such tasks performed from home. Other advantages include that the visual recognition tasks can be administered by a technician remote from the user, or the tasks can be administrated by a programmed computer.

Still other advantages to embodiments of the present invention include that the subject's performance on such tasks may be evaluated remotely by an administrator or in some instances by a computer programmed with analysis software. Other advantages include that the subject's test data may be recorded and later reviewed by researchers if there is any question about the test results, whether evaluated by an administrator or by a software algorithm implemented on a computer.

FIG. 1 illustrates a flow diagram according to an embodiment of the present invention. Initially, a subject/user directs their web browser on their computing device to a web page associated with embodiments of the present invention, step 100. In various embodiments, the user may perform this function by entering a URL, selecting a link or icon, scanning a QR code, or the like. Next, in some embodiments, the user may register their contact information to receive their results, or the like.

Next, in response to the user request, a web server provides data back to the user's device, step 110. In various embodiments, the data may include multiple images for use during the recognition task, as well as program code facilitating the recognition task, as described below. In some examples, the program code may include code that may run via the browser, e.g. Adobe Flash code, Java code, AJAX, HTML5, or like. In other examples, the program code may be a stand-alone executable application that runs upon the user's computer (Mac or PC).

Initially a series of steps are performed that provide a calibration function. More specifically, in some embodiments the front-facing camera on a user's computing system (e.g. computer, smart device, or the like) is turned on and captures images of the user, step 120. The live images are displayed back to the user on the display of the computing system, step 130. In some embodiments, a mask or other overlay is also displayed on the display, and the user is instructed to either move their head, camera, computing device, or the like, such that the user's head is within a specific region, step 140. In some examples, the mask may be a rectangular, ovoid, circular region, or the like generally within the center of a field of view of the camera.

Figure 4:
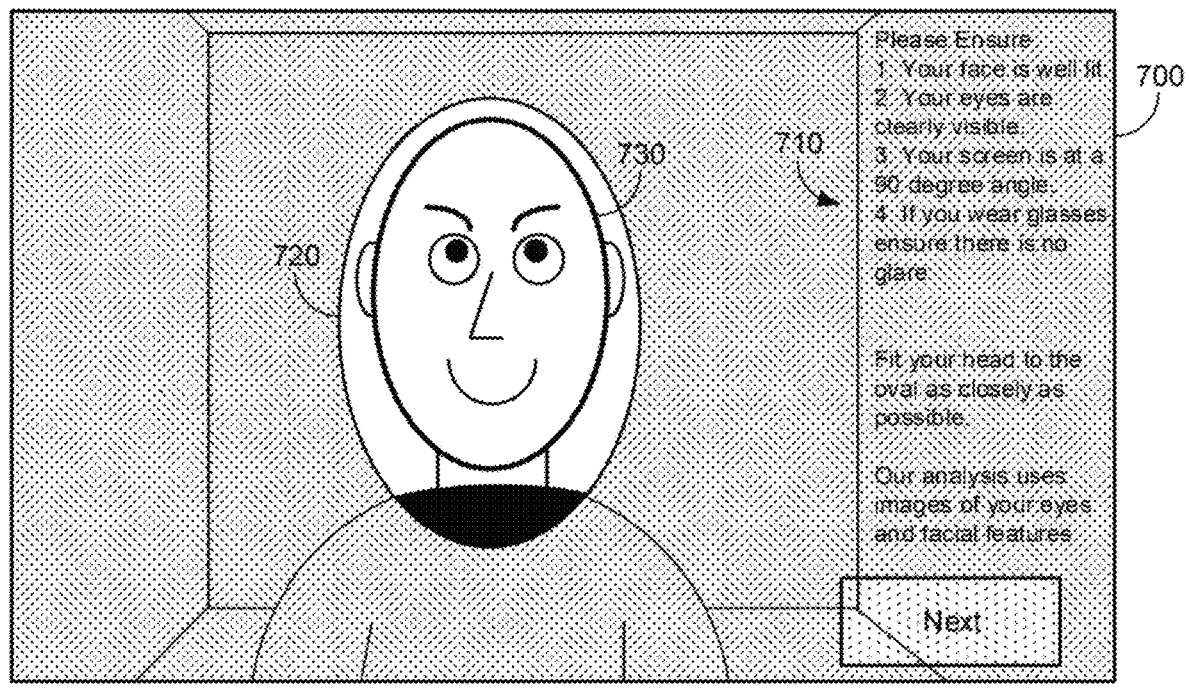
FIG. 4 is a graphical user interface of an embodiment of the present invention.

FIG. 4 illustrates an example of an embodiment of the present invention. More specifically, FIG. 4 illustrates a typical graphical user interface 700 that is displayed to a user that is mentioned in FIG. 1A, steps 130-150. As can be seen in GUI 700, the user is displayed a series of instructions 710, and an overlay frame 720. Instructions 710 instruct the user how to position their head 730 relative to overlay frame 720. In this example, the user moves their head 730 such that their head fits within overlay frame 720 before the calibration process begins.

Next, in some embodiments, a determination is made as to whether the eyes, more specifically, the pupils of the user can be clearly seen in the video images, step 150. This process may include a number of trial, error, and adjustment feedback by the computing device and the user. For example, adjustments may be made to properties of the video camera, such as gain, ISO, brightness, or the like; adjustments may include instructions to the user to increase or decrease lighting; or the like. In various embodiments, this process may include using image recognition techniques for the user's pupil against the white of the user's eye, to determine whether the pupil position can be distinguished from the white of the eye in the video. Once the system determines that the eyes can be sufficiently tracked, the user is instructed to maintain these imaging conditions for the duration of the visualization task.

As illustrated in FIG. 1, the process then includes displaying a small image (e.g. dot, icon, etc.) on the display and moving the image around the display and the user is instructed to follow the image with their eyes, step 160. In various embodiments, the locations of the dot on the display are preprogrammed and typically incudes discrete points or continuous paths along the four corners of the display, as well as near the center of the display. During this display process, a video of the user's eyes are recorded by the camera, step 170. In some embodiments, the video may be the full-frame video captured by the camera or the video may be a smaller region of the full-frame video. For example, the smaller region may be roughly the specific region mentioned in step 140, above (e.g. oval, circle, square, rectangular, etc.); the smaller region may be a specific region where the user's eyes are located (e.g. small rectangle, etc.); the smaller region may be a region capturing the face of a user (e.g. bounding rectangle, etc.); or the like. Such embodiments may be computationally advantageous by facilitating or reducing the computations and analysis performed by the user's computer system or by a remote computing system. Further, such embodiments may be advantageous by greatly reducing communications to, data storage of, and computations by the remote server. In one example, the video is captured using a video capture program called HDFVR, although any other programs (e.g. Wowza GoCoder, or the like) may be used other implementations.

Next, in various embodiments, an analysis is performed upon the video captured in step 170 based upon the display in step 160 to determine a gaze model, step 180. More specifically, the position of the user's pupil with regards to the white of the eye is analyzed with respect to the locations of the dot on the display. For example, when the dot is displayed on the upper right hand side of the display, the position of the user's pupils at the same time are recorded.

This recorded position may be used to determine a gaze model for the user. In one specific example, the dot is displayed on the four corners and the center of the display, and the corresponding positions of the user's pupils are used as principal components, e.g. eigenvector, for a gaze model for the user. In other examples, a gaze model may include a larger or smaller (e.g. two, signifying left and right) number of principal components. In other embodiments, other representations for gaze models may be used.

In various embodiments, the video (or smaller video region) is combined with metadata, and sent to a remote server (e.g. analysis server), step 190. In some examples, the metadata in embedded in the video on a frame by frame basis (e.g. interleaved), and in other examples, the metadata may be sent separately or at the end of the video. The inventor believes there are computational advantages to interleaving metadata with each respective video image compared to a separate metadata file and video image file. For example, in some embodiments eye gaze position data for a specific video image is easily obtained from metadata adjacent to that frame. In contrast, in cases of a single metadata file, the computer must maintain an index in the metadata and the video images and hope that the index synchronization is correct.

In some embodiments, the metadata may include some combination, but not necessarily all of the following data, such as: camera setting data, data associated with the user (e.g. account name, email address), browser setting data, timing data for the dots on the display, the gaze model, a determined gaze position, and the like. As examples, the data may provide a correspondence between when a dot is positioned on the upper right corner of the display and an image of how the user's eyes appear in the video at about the same time; the meta data may include timing or a series of frame numbers; or the like. In one example, the combined file or data stream may be a Flash video file, e.g. FLV, a web real-time communications file (WebRTC), or the like. Further, the remote server may be a cloud-based video server, such as a Wowza Amazon web service, or others. In one embodiment, an instance of Wowza can be used to store the uploaded all of the integrated video and metadata data discussed herein. In some embodiments, to reduce communications to, data storage of, and computations by the remote server, the frame rate of the video transferred is at the recording frame rate, e.g. 25 frames per second, 60 frames per second, or the like. however the remote server may record the video at less than the recording frame rate; in other embodiments, the frame rate of the transferred video to the remote server may be less, e.g. from about 2 to 3 frames per second up to the recording frame rate.

Next, in various embodiments, a series of steps may be performed that determine whether the gaze model is usable, or not. Specifically, the process includes displaying a small dot, similar to the above, to specific locations on the display, and the user is instructed to stare at the dot, step 200. As the user watches the dot, the video camera captures the user's eyes, step 210. Next, using the full-frame video, or a smaller region of the video, images representing the pupils of the user's eyes are determined, step 220.

In various embodiments, using principal component analysis, the images of the pupils are matched to the gaze model (e.g. eigenvectors) to determine the principal components (e.g. higher order eigenvalues) for the pupils with respect to time. As merely examples, if the user is looking to the center left of the display at a particular time, the principal components determined may be associated with the upper left and lower left of the display, from the gaze model; if the user is looking to the upper center of the display at a different time, the principal components determined may be associated with the center, the upper right and upper left of the display, from the gaze model; and the like. Other types of matching algorithms besides principal component analysis may be implemented in other embodiments of the present invention, such as least squares, regression analysis, or the like. In still other embodiments, this process may include determining one or more visual landmarks of a user's face, and pattern matching techniques to determine geometric features, e.g. position and shape of the user's eyes, locations of pupils, direction of pupil gaze, and the like. In various embodiments, if the images of the pupils corresponding to the set display positions do not match the gaze model, the process above may be repeated, step 230.

In various embodiments, similar to step 190 above, the video (or smaller video region) may be combined with metadata (e.g. timing or synchronization data, an indication of where the dot is on the screen when the image of the user's eyes are captured, and the like), and sent back to the remote server, step 240.

Once the gaze model is validated, a series of steps providing a familiarization phase are performed. More specifically, in some embodiments, one or more images are displayed to the user on the display, step 250. In some examples, the images are one that were provided to the user's computing system in step 110, and in other examples, (e.g. using AJAX), the images are downloaded on-demand, e.g. after step 110.

In various embodiments, the images are specifically designed for this visualization task. In one example, the images are all binary images including objects in black over a white background, although other examples may have different object and background colors. In some embodiments, the images may be gray scale images (e.g. 4-bit, 8-bit, etc.), or color images (e.g. 4-bit color, or greater). Further, in some embodiments, the images are static, whereas in other embodiments, the images may be animated or moving. Additionally, in some embodiments, images designed for this visualization task are specifically designed to have a controlled number of geometric regions of interest (e.g. visual saliency).

The number of geometric regions of interest may be determined based upon experimental data, manual determination, or via software. For example, to determine experimental data, images may be displayed to a number of test subjects, and the locations on the image where the test subjects eyes linger upon for over a threshold amount of time may be considered a geometric region of interest. After running such experiments, test images may become identifiable via the number of geometric regions of interest. As an example, an image of a triangle may be characterized by three regions of interest (e.g. the corners), and an image of a smiley face may be characterized by four regions of interest (e.g. the two eyes, and the two corners of the mouth). In other embodiments, geometric regions of interest may be determined using image processing techniques such as Fourier analysis, morphology, or the like. In some embodiments, the images presented to the user, described below, may each have the same number of regions of interest, or may have different numbers of regions of interest, based upon specific engineering or research purposes.

In some embodiments, an image is displayed to the left half of the display and to the right half of the display for a preset amount of time. The amount of time may range from about 2 seconds to about 10 seconds, e.g. 5 seconds. In other embodiments, different pairs of images may be displayed to the user during this familiarization phase trial.

During the display of the images, the video camera captures the user's eyes, step 260. Next, using the full-frame video, or a smaller region of the video, images representing the pupils of the user's eyes are determined. In some embodiments, using principal component analysis, or the like, of the gaze model, the gaze position of the user's eyes are determined with respect to time, step 280. In various embodiments, similar to step 190 above, the video (or smaller video region) may be combined with metadata (e.g. including an indication of what is displayed on the screen at the time the specific image of the user's eyes is captured, etc.), and the data, or portions of the data may be sent back to the remote server, step 290. In another embodiment, the video (or smaller video region) may be combined with metadata (e.g. including an indication of what is displayed on the screen at the time the specific image of the user's eyes is captured, etc.), and processed on the user's device (e.g., computer, phone).

In various embodiments, this process may then repeat for a predetermined number of different pictures (or iterations), step 300. In some examples, the process repeats until a predetermined number sets of images are displayed. In some embodiments, the predetermined number is within a range of 10 to 20 different sets, within a range of 20 to 30 different sets, within a range of 30 to 90 different sets, although different numbers of trials are contemplated. In some embodiments, the familiarization phase may take about 1 to 3 minutes, although other durations can be used, depending upon desired configuration.

Subsequent to the familiarization phase, a series of steps providing a test phase are performed. More specifically, in some embodiments, one image that was displayed within the familiarization phase is displayed to user along with a novel image (that was not displayed within the familiarization phase) on the display, step 310. Similar to the above, in some examples, the novel images are ones that were provided to the user's computing system in step 110, whereas in other examples, (e.g. using AJAX), the images are downloaded on-demand, e.g. after step 110. In some embodiments, the novel images may be variations of or related to the familiar images that were previously provided during the familiarization phase. These variations or related images may be visually manipulated versions of the familiar images. In some examples, the novel images may be the familiar image that is rotated, distorted (e.g. stretched, pin cushioned), resized), filtered, flipped, and the like, and in other examples, the novel images may be the familiar image that have slight changes, such as subtraction of a geometric shape (e.g. addition of a hole), subtraction of a portion of the familiar image (e.g. removal of a leg of a picture of a table), addition of an extra geometric feature (e.g. adding a triangle to an image), and the like. In various embodiments, the manipulation may be performed on the server and provided to the user's computing system, or the manipulation may be performed by the user's computing system (according to directions from the server).

In various embodiments, the novel images are also specifically designed to be similar to the images during the familiarization phase in appearance (e.g. black over white, etc.) and are designed to have a controlled number of geometric regions of interest. As an example, the novel images may have the same number of geometric regions of interest, a higher number of geometric regions of interest, or the like.

During the display of the novel and familiar images, the video camera captures the user's eyes, step 320. Next, using the full-frame video, or a smaller region of the video, images representing the pupils of the user's eyes are optionally determined. In various embodiments, using principal component analysis, or the like, of the gaze model, the gaze position of the user's eyes are determined with respect to time, step 340.

In some embodiments, based upon the gaze position of the user's eyes during the display of the novel image and the familiar image (typically with respect to time), a determination is made as to whether the user gazes at the novel image for a longer duration compared to the familiar image, step 350. In some embodiments, a preference for the novel image compared to the familiar image may be determined based upon gaze time (51% novel to 49% familiar); a threshold gaze time (e.g. 60% novel to 40% familiar, or the like); based upon gaze time in combination with a number of geometric regions of interests (e.g. 4 novel versus 3 familiar); based upon speed of the gaze between geometric regions of interest (e.g. 30 pixels/second novel versus 50 pixels/second familiar); or the like. In light of the present patent disclosure, other types of gaze factors and other proportions of novel versus familiar may be computed. In various embodiments, the novel image or familiar image preference is stored as metadata, step 360. In various embodiments, similar to step 190 above, the video (or smaller video region) may be combined with metadata (e.g. an indication of which images are displayed on the right-side or left-side of the display, etc.), and sent back to the remote server, step 370.

In various embodiments, this process may then repeat for a predetermined number of different sets of novel and familiar images, step 380. In some examples, the testing phase process repeats until 10 to 20 different sets of images (e.g. iterations) are displayed to the user, although different numbers of trials (e.g. 20 to 30 iterations, etc.) are also contemplated. In some embodiments, novel images that are displayed may have an increasing or decreasing number of geometric regions of interest as the test phase iterates, depending upon performance of the user. For example, if a gaze of a user is not preferencing the novel image over the familiar image, the next novel image displayed to the user may have a greater number of geometric regions of interest, and the like. Other types of dynamic modifications may be made during the test phase depending upon user performance feedback.

In some embodiments, after the test phase, the gaze position data may be reviewed to validate the scores, step 385. In some embodiments, the gaze position data with respect to time may be reviewed and/or filtered to remove outliers and noisy data. For example, if the gaze position data indicate that a user never looks at the right side of the screen, the gaze model is probably incorrect calibrated, thus the gaze model and gaze data may be invalidated; if the gaze position data indicate that the user constantly looks left and right on the screen, the captured video may be too noisy for the gaze model to distinguish between the left and the right, thus the gaze position data may be invalidated; or the like. In various embodiments, the gaze position data may not only be able to track right and left preference, but in some instances nine or more different gaze positions on the display. In such cases, the gaze position data (for example, a series of (x,y) coordinate pairs), may be filtered in time, such the filtered gaze position data is smooth and continuous on the display. Such validation of gaze position data may automatically performed, or in some cases, sub-optimally, by humans.

In various embodiments, after data validation, the preferencing data determined above in step 350 and or in step 385 may be used to determine a cognitive performance score for the user, step 390. For example, if the user shows a preference for the novel image over the familiar image for over about 70% of the time (e.g. 67%), the user may be given a passing or success score; if the user has a preference of over about 50% (e.g. 45%) but less than about 70% (e.g. 67%), the may be given a qualified passing score; if the user has no preference, e.g. less than about 50% (e.g. 45%) the user may be given an at risk score or not successful score. In some embodiments, based upon an at-risk user's score, a preliminary diagnosis indicator (e.g. what cognitive impairment they might have) may be given to the user. The number of classifications as well as the ranges of preference may vary according to specific requirements of various embodiments of the present invention. In some embodiments where step 390 is performed on the user's computer, this data may also be uploaded to the remote server, whereas if step 390 is performed on a remote server, this data may be provided to the user's computer. In some embodiments, the uploaded data is associated with the user in the remote server. It is contemplated that the user may request that the performance data be shared with a health care facility via populating fields in the user's health care records, or on a social network.

In some embodiments of the present invention, the user's computer system may be programmed to perform none, some, or all of the computations described above (e.g. calibration phase, validation phase, familiarization phase, and/or test phase). In cases where not all of the computations are performed by the user's computer system, a remote server may process the uploaded data based upon the video images and metadata, e.g. timing, synchronization data, indication of which images are displayed on the right-side and the left-side of the display at the time the image of the user's eyes is captured, and the like. In some embodiments, the remote server may return the computed data, e.g. gaze model and principal component analysis results, to the user's computer system, whereas in other embodiments, such computed data is only maintained by the remote server.

In various embodiments the computations performed within the test phase to determine the preferencing between the novel image compared to the familiar image may also be partially or completely performed on the user's computer and/or by the remote server. In some embodiments, the determination of preferencing may be made by determining a number of frames having principal components (or other algorithm) of the novel image compared to the number of frames having principal components (or other algorithm) of the familiar image. For example, if the percentage of frames within a test phase, based upon the user's gaze position, where the user is looking at the novel image exceeds a threshold, the user may be considered to successfully pass the test.

In other embodiments, the evaluation of whether the user is looking at the novel image or the familiar image may be performed by one or more individuals coupled to the remote server. For example, administrators may be presented with the video images of the user's eyes, and based upon their human judgment, the administrator may determine whether the user is looking to the left or to the right of the display, whether the user is blinking, whether the image quality is poor, and the like. This determination is then combined by the remote server with the indication of whether the novel image is displayed on the left or the right of the display, to determine whether which image the user is looking at during the human-judged frame. In some initial tests, three or more administrators are used so a majority vote may be taken. The inventor is aware that manual intervention may raise the issue of normal variability of results due to subjectivity of the individuals judging the images as well as of the user taking the test, e.g. fatigue, judgment, bias, emotional state, and the like. Such human judgments may be more accurate in some respects, as humans can read and take into accounts emotions of the user. Accordingly, automated judgments made by algorithms run within the remote server may be less reliable in this respect, as algorithms to attempt to account for human emotions are not well understood.

In some embodiments, the process above may be implemented as a game, where the user is not told of the significance of the images or the testing. In such embodiments, feedback may be given to the user based upon their success in having a preference of the novel image, step 410. As examples of user feedback may include: a sound being played such as: a triumphant fanfare, an applause, or the like; a running score total may increment and when a particular score is reached a prize may be sent (via mail) to the user; a video may be played; a cash prize may awarded to the user; a software program may become unlocked or available for download to the user; ad-free streaming music may be awarded; tickets to an event may be awarded; access to a VIP room; or the like. In light of the present patent disclosure, one of ordinary skill in the art will recognize many other types of feedback to provide the user in other embodiments of the present invention.

In other embodiments of the present invention, if the user is identified as not being successful or at risk, the user is identified as a candidate for further testing, step 420. In various embodiments, the user may be invited to repeat the test; the user may be invited to participate in further tests (e.g. at a testing facility, office, lab); the user may be given information as to possible methods to improve test performance; the user may be invited to participate in drug or lifestyle studies; the user may be awarded a care package; or the like. In light of the present patent disclosure, one of ordinary skill in the art will recognize many other types of feedback to provide the user in other embodiments of the present invention. Such offerings for the user may be made via electronic communication, e.g. e-mail, text, via telephone call, video call, physical mail, social media, or the like. Step 430. In other embodiments, prizes, gifts, bonuses, or the like provided in step 410 may also be provided to the user in step 430.

In one embodiment, the user is automatically enrolled into cognitive decline studies, step 440. As part of such studies, the user may take experimental drugs or placebos, step 450. Additionally, or instead, as part of such studies, the user may make lifestyle changes, such as increasing their exercise, changing their diet, playing cognitive games (e.g. crossword puzzles, brain-training games, bridge, or the like.), reducing stress, adjusting their sleeping patterns, and the like. In some embodiments, the user may also be compensated for their participation in such studies by reimbursement of expenses, payment for time spent, free office visits and lab work, and the like.

In various embodiments, the user may periodically run the above-described operations to monitor their cognitive state over time, step 460. For example, in some embodiments, the user may take the above test every three to six months (the first being a baseline), and the changes in the user's performance may be used in steps 390 and 400, above. More specifically, if the user's percentage preference for the novel image drops by a certain amount (e.g. 5%, 10%, etc.) between the tests, step 400 may not be satisfied, and the user may be identified for further testing.

In other embodiments of the present invention, various of the above described steps in FIGS. 1A-1E may be performed by a remote server, and not the user's computer (e.g. client). As examples: step 180 may be performed after step 190 in the remote server; steps 220 and 230 may be performed after step 240 in the remote server; step 280 may be performed after step 290 in the remote server; steps 340-360 may be performed after step 370 on the remote server; steps 390-400 may be performed in the remote server; steps 410-440 may be performed, in part, by the remote server; and the like. The division of the processing may be made between the user's computer and the remote server based upon engineering requirements or preferences, or the like.

Figure 2:
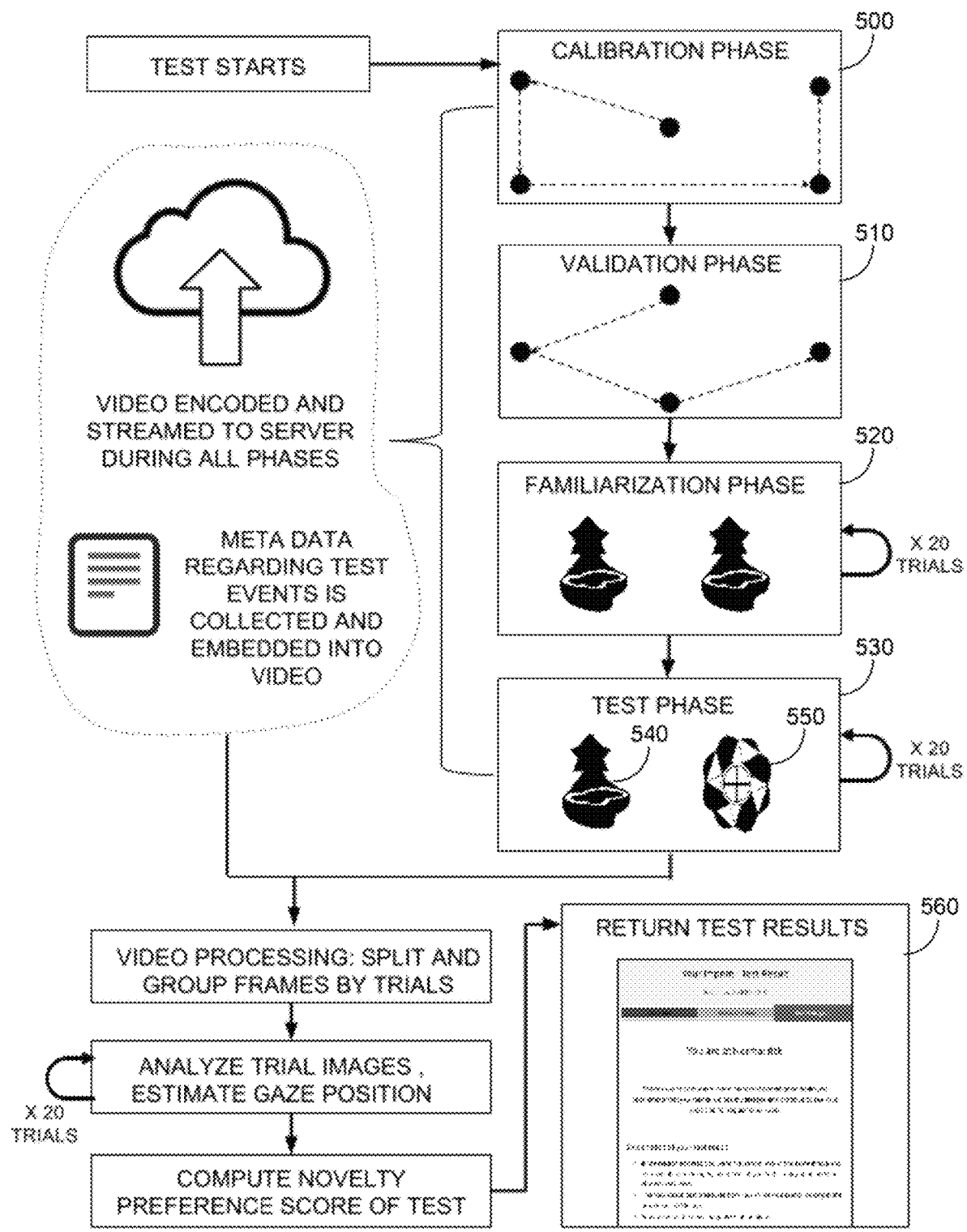
FIG. 2 is a simplified diagram of a process according to an embodiment of the present invention.

FIG. 2 is a simplified diagram of a process according to an embodiment of the present invention. More specifically, FIG. 2 illustrates examples of an image 500 that may be displayed to the subject within the calibration phase; examples of an image 510 that may be displayed to the subject within the validation phase; examples of familiar images 520 that may be displayed to the subject within the familiarization phase; and examples of an image 530 that may be displayed to the subject within the test phase including a familiar image 540 and a novel image 550. Additionally, as shown in FIG. 2, an example 560 of feedback given to the user is shown. Some embodiments, the feedback may be instantaneous, or arrive later in the form of an electronic or physical message, or the like.

In other embodiments of the present invention, other types of eye tracking task paradigms and studies may be performed besides the ones describe above, such as: attention and sequencing tasks, set-shifting tasks, visual discrimination tasks, and emotional recognition, bias tasks, and the like. Additional studies may include processing of additional biological information including blood flow, heart rate, pupil diameter, pupil dilation, pupil constriction, saccade metrics, and the like. The process through which biological data and cognitive task performance is collected may be similar to one of the embodiments described above. Additionally, scoring procedures can determine the location and change over time of various landmarks of the participant's face (e.g., pupil diameter, pupil dilation). These procedures can also estimate the eye gaze position of each video frame.

Figure 3:
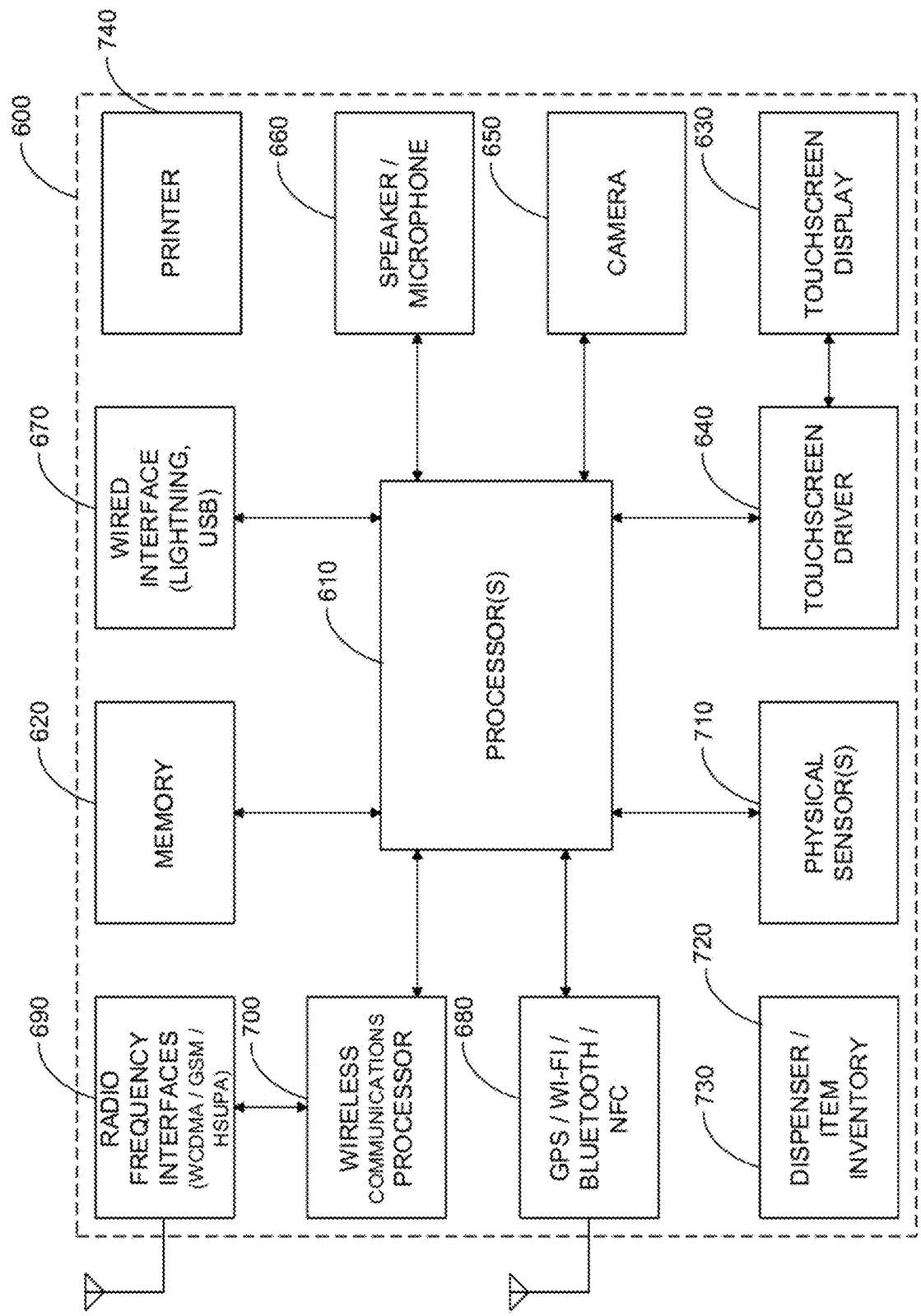
FIG. 3 is a block diagram of typical computer system according to various embodiment of the present invention.

FIG. 3 illustrates a functional block diagram of various embodiments of the present invention. A computer system 600 may represent a desktop or lap top computer, a server, a smart device, tablet, a smart phone, or other computational device. In FIG. 3, computing device 600 may include an applications processor 610, memory 620, a touch screen display 630 and driver 640, an image acquisition device (e.g. video camera) 650, audio input/output devices 660, and the like. Additional communications from and to computing device are typically provided by via a wired interface 670, a GPS/Wi-Fi/Bluetooth interface 680, RF interfaces 690 and driver 700, and the like. Also included in some embodiments are physical sensors 710.

In various embodiments, computing device 600 may be a hand-held computing device (e.g. Apple iPad, Amazon Fire, Microsoft Surface, Samsung Galaxy Noe, an Android Tablet); a smart phone (e.g. Apple iPhone, Motorola Moto series, Google Pixel, Samsung Galaxy S); a portable computer (e.g. Microsoft Surface, Lenovo ThinkPad, etc.), a reading device (e.g. Amazon Kindle, Barnes and Noble Nook); a headset (e.g. Oculus Rift, HTC Vive, Sony PlaystationVR) (in such embodiments, motion tracking of the head may be used in place of, or in addition to eye tracking); or the like.

Typically, computing device 600 may include one or more processors 610. Such processors 610 may also be termed application processors, and may include a processor core, a video/graphics core, and other cores. Processors 610 may be a processor from Apple (e.g. A9, A10), NVidia (e.g. Tegra), Intel (Core, Xeon), Marvell (Armada), Qualcomm (Snapdragon), Samsung (Exynos), TI, NXP, AMD Opteron, or the like. In various embodiments, the processor core may be based upon an ARM Holdings processor such as the Cortex or ARM series processors, or the like. Further, in various embodiments, a video/graphics processing unit may be included, such as an AMD Radeon processor, NVidia GeForce processor, integrated graphics (e.g. Intel) or the like. Other processing capability may include audio processors, interface controllers, and the like. It is contemplated that other existing and/or later-developed processors may be used in various embodiments of the present invention.

In various embodiments, memory 620 may include different types of memory (including memory controllers), such as flash memory (e.g. NOR, NAND), pseudo SRAM, DDR SDRAM, or the like. Memory 620 may be fixed within computing device 600 or removable (e.g. SD, SDHC, MMC, MINI SD, MICRO SD, CF, SIM). The above are examples of computer readable tangible media that may be used to store embodiments of the present invention, such as computer-executable software code (e.g. firmware, application programs), application data, operating system data, images to display to a subject, or the like. It is contemplated that other existing and/or later-developed memory and memory technology may be used in various embodiments of the present invention.

In various embodiments, touch screen display 630 and driver 640 may be based upon a variety of later-developed or current touch screen technology including resistive displays, capacitive displays, optical sensor displays, electromagnetic resonance, or the like. Additionally, touch screen display 630 may include single touch or multiple-touch sensing capability. Any later-developed or conventional output display technology may be used for the output display, such as IPS-LCD, OLED, Plasma, or the like. In various embodiments, the resolution of such displays and the resolution of such touch sensors may be set based upon engineering or non-engineering factors (e.g. sales, marketing). In some embodiments of the present invention, a display output port may be provided based upon: HDMI, DVI, USB 3.X, DisplayPort, or the like.

In some embodiments of the present invention, image capture device 650 may include a sensor, driver, lens and the like. The sensor may be based upon any later-developed or convention sensor technology, such as CMOS, CCD, or the like. In some embodiments, multiple image capture devices 650 are used. For example, smart phones typically have a rear-facing camera, and a front-facing camera (facing the user, as the viewer views the display. In various embodiments of the present invention, image recognition software programs are provided to process the image data. For example, such software may provide functionality such as: facial recognition, head tracking, camera parameter control, eye tracking or the like as provided by either the operating system, embodiments of the present invention, or combinations thereof.

In various embodiments, audio input/output 660 may include conventional microphone(s)/speakers. In some embodiments of the present invention, three-wire or four-wire audio connector ports are included to enable the user to use an external audio device such as external speakers, headphones or combination headphone/microphones. In some embodiments, this may be performed wirelessly. In various embodiments, voice processing and/or recognition software may be provided to applications processor 610 to enable the user to operate computing device 600 by stating voice commands. Additionally, a speech engine may be provided in various embodiments to enable computing device 600 to provide audio status messages, audio response messages, or the like.

In various embodiments, wired interface 670 may be used to provide data transfers between computing device 600 and an external source, such as a computer, a remote server, a storage network, another computing device 600, or the like. Such data may include application data, operating system data, firmware, embodiments of the present invention, or the like. Embodiments may include any later-developed or conventional physical interface/protocol, such as: USB 2.x or 3.x, micro USB, mini USB, Firewire, Apple Lightning connector, Ethernet, POTS, or the like. Additionally, software that enables communications over such networks is typically provided.

In various embodiments, a wireless interface 680 may also be provided to provide wireless data transfers between computing device 600 and external sources, such as remote computers, storage networks, headphones, microphones, cameras, or the like. As illustrated in FIG. 3, wireless protocols may include Wi-Fi (e.g. IEEE 802.11 x, WiMax), Bluetooth, IR, near field communication (NFC), ZigBee and the like.

GPS receiving capability may also be included in various embodiments of the present invention, however is not required. As illustrated in FIG. 3, GPS functionality is included as part of wireless interface 680 merely for sake of convenience, although in implementation, such functionality may be performed by circuitry that is distinct from the Wi-Fi circuitry and distinct from the Bluetooth circuitry.

Additional wireless communications may be provided via additional RF interfaces 690 and drivers 700 in various embodiments. In various embodiments, RF interfaces 690 may support any future-developed or conventional radio frequency communications protocol, such as CDMA-based protocols (e.g. WCDMA), G4, GSM-based protocols, HSUPA-based protocols, or the like. In the embodiments illustrated, driver 700 is illustrated as being distinct from applications processor 610. However, in some embodiments, these functionality are provided upon a single IC package, for example the Marvel PXA330 processor, and the like. It is contemplated that some embodiments of computing device 600 need not include the RF functionality provided by RF interface 690 and driver 700.

FIG. 3 also illustrates that various embodiments of computing device 600 may include physical sensors 710. In various embodiments of the present invention, physical sensors 710 are multi-axis Micro-Electro-Mechanical Systems (MEMS). Physical sensors 710 may include three-axis sensors (linear, gyro or magnetic); three-axis sensors (linear, gyro or magnetic); six-axis motion sensors (combination of linear, gyro, and/or magnetic); ten-axis sensors (linear, gyro, magnetic, pressure); and various combinations thereof. In various embodiments of the present invention, conventional physical sensors 710 from Bosch, STMicroelectronics, Analog Devices, Kionix, Invensense, mCube, or the like may be used.

In some embodiments, computing device 600 may include a printer 740 for providing printed media to the user. Typical types of printers may include an ink jet printer, a laser printer, a photographic printer (e.g. Polaroid-type instant photos), or the like. In various embodiments, printer 740 may be used to print out textual data to the user, e.g. instructions; print out photographs for the user, e.g. self-portraits; print out tickets or receipts that include custom bar codes, e.g. QR codes, URLs, etc.; or the like.

In various embodiments, any number of future developed or current operating systems may be supported, such as iPhone OS (e.g. iOS), Windows, Google Android, or the like. In various embodiments of the present invention, the operating system may be a multi-threaded multi-tasking operating system. Accordingly, inputs and/or outputs from and to touch screen display 630 and driver 640 and inputs/or outputs to physical sensors 710 may be processed in parallel processing threads. In other embodiments, such events or outputs may be processed serially, or the like. Inputs and outputs from other functional blocks may also be processed in parallel or serially, in other embodiments of the present invention, such as image acquisition device 650 and physical sensors 710.

In some embodiments, such as a kiosk-type computing device 600, a dispenser mechanism 720 may be provided, as well as an inventory of items 730 to dispense. In various examples any number of mechanisms may be used to dispense an item 730, such as: a gum-ball-type mechanism (e.g. a rotating template), a snack-food vending-machine-type mechanism (e.g. rotating spiral, sliding doors, etc.); a can or bottle soft-drink dispensing mechanism; or the like. Such dispensing mechanisms are under the control of processor 610. With such embodiments, a user may walk up to the kiosk and interact with the process described in FIGS. 1A-1E. Based upon the test results, processor may activate the dispenser mechanism 720 and dispense one or more of the items 730 to the user in FIG. 1E, steps 410, 430, 440 or 450.

FIG. 3 is representative of one computing device 600 capable of embodying the present invention. It will be readily apparent to one of ordinary skill in the art that many other hardware and software configurations are suitable for use with the present invention. Embodiments of the present invention may include at least some but need not include all of the functional blocks illustrated in FIG. 3. For example, in various embodiments, computing device 600 may lack touchscreen display 1130 and touchscreen driver 1140, or RF interface 690 and/or driver 700, or GPS capability, or the like. Additional functions may also be added to various embodiments of computing device 600, such as a physical keyboard, an additional image acquisition device, a trackball or trackpad, a joystick, an internal power supply (e.g. battery), or the like. Further, it should be understood that multiple functional blocks may be embodied into a single physical package or device, and various functional blocks may be divided and be performed among separate physical packages or devices.

In some embodiments of the present invention, computing device 600 may be a kiosk structure. Further, in some instances the kiosk may dispense an item, such as a placebo drug, a drug study medication, different types of foods (e.g. snacks, gum, candies), different types of drinks (e.g. placebo drink, drug study drink), and the like. In some instances, an item may be informational data printed by printer 740 related to the performance of the user (e.g. life style advice, eating well information, etc.). In additional instances, an item (e.g. a ticket or stub) may include a custom URL, bar code (e.g. 2D bar code, QR code), or the like, that links to a web site that is has access to the user's test results. It is contemplated that the linked site may be associated with a testing organization, a drug study site associated with a pharmaceutical company, a travel web site, an e-commerce web site, or the like. In such cases, for privacy purposes, it is contemplated that the user will remain anonymous to the linked site, until the user chooses to register their information. In still other instances, an item may be a picture of the user (e.g. a souvenir photo, a series of candid photographs, or the like), in some instances in conjunction with the informational data or link data described above. In yet other embodiments, the kiosk may be mobile, and the kiosk may be wheeled up to users, e.g. non-ambulatory users.

Having described various embodiments and implementations, it should be apparent to those skilled in the relevant art that the foregoing is illustrative only and not limiting, having been presented by way of example only. For example, in some embodiments, a user computing device may be a tablet or a smart phone, and a front facing camera of such a device may be used as the video capture device described herein. Additionally, the various computations described herein may be performed by the tablet or smart phone alone, or in conjunction with the remote server. Many other schemes for distributing functions among the various functional elements of the illustrated embodiment are possible. The functions of any element may be carried out in various ways in alternative embodiments.

Also, the functions of several elements may, in alternative embodiments, be carried out by fewer, or a single, element. Similarly, in some embodiments, any functional element may perform fewer, or different, operations than those described with respect to the illustrated embodiment. Also, functional elements shown as distinct for purposes of illustration may be incorporated within other functional elements in a particular implementation. Also, the sequencing of functions or portions of functions generally may be altered. Certain functional elements, files, data structures, and so one may be described in the illustrated embodiments as located in system memory of a particular computer. In other embodiments, however, they may be located on, or distributed across, computer systems or other platforms that are co-located and/or remote from each other. For example, any one or more of data files or data structures described as co-located on and "local" to a server or other computer may be located in a computer system or systems remote from the server. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures of files may be used and various described data structures of files may be combined or otherwise arranged.

Further embodiments can be envisioned to one of ordinary skill in the art after reading this disclosure. For example, some embodiments may be embodied as a turn-key type system such as a laptop or kiosk with executable software resident thereon. The software is executed by the processor of the laptop and provides some, if not all, of the functionality described above in FIGS. 1A-1E, such as: calibration of the web camera to the subject's face and/or eyes, determination of a gaze model, outputting of the familiar and test images at the appropriate times, determining the gaze of the subject for familiar and test images with respect to time during the test using the gaze model, and the like. The subject test data may be stored locally on the laptop and/or be uploaded to a remote server.

In various embodiments, features, other than just the gaze position for the user may be utilized. For example, facial expressions (e.g. eyebrows, lip position, etc.) as well as hand placements and gestures of a user may also be considered (e.g. surprise, puzzled, anger, bewilderment, etc.) when determining whether the cognitive performance of a user. In other embodiments, additional eye-related factors may also be detected and used, such as: blink rate of the user, pupil dilation, pupil responsiveness (e.g. how quickly the pupil dilates in response to a flash on the display), saccadic movement, velocity, and the like.

In still other embodiments, the method performs a treatment or further analysis using information from the analysis and/or diagnostic methods described above. In an example, the treatment or further analysis can include, an MRI scan, CAT scan, x-ray analysis, PET scans, a spinal tap (cerebral spinal fluid) test (amyloid plaque, tau protein), a beta-amyloid test, an MRT blood test, and others. In order to initiate any of the analysis and/or diagnostic method includes using the information to open a lock or interlock to initiate the analysis and/or diagnostic method. In an example, treatment can include automated or manual administration of a drug or therapy.

As an example discussed above, in kiosk embodiments, the treatment includes using the user's cognitive performance information to access the drug, which is under a lock or secured container, and to dispense the drug. In another example, a PET/MRI scans are provided for an amyloid plaque. In an example, the treatment can include a spinal tap for cerebral spinal fluid to measure amyloid plague and tau (protein believed to be involved in Alzheimer's disease). Of course, there can be other variations, modifications, and alternatives. In yet another example, treatment can include a physician that places the patient on an Alzheimer's drug such as Namenda™, Exelon™, among others. In an example, the patient can be treated using wearable devices such as a Fitbit™ to track exercise, movement, and sleep activity.

In an example, the method provides results that are preferably stored and secured in a privileged and confidential. In an example, the results and/or information is secured, and subject to disclosure only by unlocking a file associated with the information. In an example, a physician or health care expert can access the results after the security is removed.

In an example, the image can also be configured to capture another facial element. The facial element can include a mouth, nose, cheeks, eye brows, ears, or other feature, or any relations to each of these features, which can be moving or in a certain shape and/or place, to identify other feature elements associated with an expression or other indication of the user. Of course, there can be other variations, modifications, and alternatives.

In an example, the image can also be configured to capture another element of known shape and size as a reference point. In an example, the element can be a fixed hardware element, a piece of paper, or code, or other object, which is fixed and tangible. As an example, a doctor, pharmaceutical, or the like may provide the user with a business card or other tangible item, that has a unique QR code imprinted thereon. In various embodiments, the user may display the QR code to the camera, for example in FIG.

1A, step 120. In other embodiments, the remote server may use the QR code to determine a specific version of the cognitive test described therein and provide specific prizes, gifts, and information to the user. As an example, Pharmaceutical A may have a 6 minute visual test, based upon colored images, whereas Researchers B may have a 5 minute visual test, based upon black and white images, etc. It should be understood that many other adjustments may be made to the process described above, and these different processes may be implemented by a common remote server. Of course, there can be other variations, modifications, and alternatives.

In other examples, the present technique can be performed multiple times. In an example, the multiple times can be performed to create a baseline score. Once the base line score is stored, and other tests can be performed at other times to reference against the base line score. In an example, the base line score is stored into memory on a secured sever or client location. The base line score can be retrieved by a user, and then processed along with new test scores to create additional scores. Of course, there can be other variations, modifications, and alternatives.

In an alternative example, the present technique can be used to identify other cognitive diseases or other features of the user, such as: anxiety, stress, depression, suicidal tendencies, childhood development, and the like. In an example, the technique can be provided on a platform for other diseases. The other diseases can be provided on various modules, which are included. In still other embodiments, the disclosed techniques may be used as a platform for other user metrics, e.g. user motion or gait capture and analysis, user pose or posture analysis. Embodiments may be located at hospitals and when users take the test and fail to show sufficient novelty preference, a directory of specific doctors or departments may become unlocked to them. Users who show sufficient novelty preference may not have access to such providers.

In some embodiments, user response to different pictures may be used for security purposes (e.g. TSA, CIA, FBI, police) or the like. As an example, during a testing phase, the user may be displayed a familiar image that is neutral, such as a flower or stop sign, and be displayed a novel image that illustrates violence, such as an AK-47 gun, a bomb, a 9-11 related image, or the like. In some cases, deliberately avoids looking at the novel image may be considered a security risk. Other embodiments may be used in motor vehicle department for determining whether older drivers have sufficient cognitive performance to safely handle a vehicle.

In some examples, algorithms may be implemented to determine whether a user is attempting to fool the system. For example, gaze analysis maybe used to determine if the user is trying to cover up a cognitive shortcoming.

In an example, the present technique can be implemented on a stand-alone kiosk. In an example, the camera and other hardware features, can be provided in the kiosk, which is placed strategically in a designated area. The kiosk can be near a pharmacy, an activity, or security zone, among others. In an example, the technique unlocks a dispenser to provide a drug, the technique unlocks a turnstile or security gate, or the like, after suitable performance of the technique. Of course, there can be other variations, modifications, and alternatives.

In an example, the technique can also be provided with a flash or other illumination technique into each of the eyes.

In other embodiments, combinations or sub-combinations of the above disclosed invention can be advantageously made. The block diagrams of the architecture and flow charts are grouped for ease of understanding. However it should be understood that combinations of blocks, additions of new blocks, re-arrangement of blocks, and the like are contemplated in alternative embodiments of the present invention. Further examples of embodiments of the present invention are provided in the attached appendix.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed:

1. A method of processing information including aligning eye movement with an image capturing device for detection of cognitive anomalies, the method comprising:
    initiating an application, under control of a processor, to output an image of a frame on a display device to a user, the display device being coupled to the processor, the processor being coupled to a communication device coupled to a network of computers, the network of computers being coupled to a server device;
    initiating a camera coupled to the application to capture a video image of a head of a user, the head of the user being positioned by the user viewing the display device;
    displaying the video of the image of the head of the user on the display device within a vicinity of the frame being displayed;
    positioning the head of the user within the frame to align the head to the frame, and capturing an image of the head of the user;
    processing captured information regarding the image of the head to initiate an image capturing process of eye movement of the user;
    outputting an indication on a display after initiation of the image capturing process; and moving the indication spatially to one of a plurality of images being displayed on the display device;
    capturing a video of each eye of the human user, while the head is maintained at an approximately stationary spatial position relative to the camera, and each of the eyes moves to track the position of the indication of the display, the image of each eye comprising a sclera portion, an iris portion, and a pupil portion;
    parsing the video to determine a first reference image corresponding to a first eye position for a first spatial position for the indication; and a second reference image corresponding to a second eye position for a second spatial position of the indication; and
    correlating each of the other plurality of images to either the first reference image or the second reference image.

2. The method of claim 1 wherein the parsing of the video occurs at the server device; and further comprising transferring the video of each eye of the human user through the network to the server device.

3. The method of claim 1 wherein the parsing of the video occurs at a user's device.

4. The method of claim 1 further comprising illuminating each of the eyes to highlight a position of each iris portion in reference to the respective sclera portion.

5. The method of claim 1 further comprising illuminating each of the eyes to highlight a position of each iris portion in reference to the respective sclera portion to cause an iris pixel image of each iris portion and a sclera pixel image of the respective sclera portion to have a contrast ratio of about 1:1 to about 1:10.

6. The method of claim 1 wherein the camera is characterized by a sub-megapixel resolution.

7. The method of claim 1 further comprising transferring the plurality of images from a storage device coupled to the processing device, each of the plurality of images comprising identification information.

8. The method of claim 1 further comprising processing the captured video to include the identification information, and transferring the captured video including the identification information through the network of computers to the server device.

9. The method of claim 1 parsing the captured video to identify a reference image; processing the reference image to determine whether an iris pixel image and the related sclera pixel image is within a selected contrast ratio.

10. The method of claim 9 further comprising:
providing feedback to the user regarding improving video capture conditions in response to the iris pixel image and the related sclera pixel image not being within the selected contrast ratio.

* * * * *